(12) United States Patent
Ruedinger et al.

(10) Patent No.: US 6,281,385 B1
(45) Date of Patent: Aug. 28, 2001

(54) PROCESS FOR PREPARING ACETIC ACID BY GAS-PHASE OXIDATION OF SATURATED C4-HYDROCARBONS AND THEIR MIXTURES WITH UNSATURATED C4-HYDROCARBONS

(75) Inventors: Christoph Ruedinger; Hans-Juergen Eberle, both of München (DE)

(73) Assignee: Consortium für elektrochemische Industrie GmbH, Munich (DE)

( * ) Notice: Subject to any disclaimer, the term of this patent is extended or adjusted under 35 U.S.C. 154(b) by 0 days.

(21) Appl. No.: 09/313,398

(22) Filed: May 18, 1999

(30) Foreign Application Priority Data

May 22, 1998 (DE) ................................ 198 23 052

(51) Int. Cl.$^7$ .................................... C07C 51/21
(52) U.S. Cl. ................ 562/548; 562/512.2; 562/607
(58) Field of Search .................. 562/548, 512.2, 562/607

(56) References Cited

U.S. PATENT DOCUMENTS

| | | |
|---|---|---|
| 3,464,930 | 9/1969 | Friedrichsen et al. . |
| 3,917,682 | 11/1975 | Mizukami et al. . |
| 3,948,807 * | 4/1976 | Fuchigami et al. . |
| 3,954,857 | 5/1976 | Brockhaus . |
| 4,066,704 | 1/1978 | Harris et al. . |
| 4,113,660 * | 9/1978 | Abe et al. . |
| 4,146,734 | 3/1979 | Slinkard . |
| 4,195,188 * | 3/1980 | Slinkard et al. . |
| 4,219,671 * | 8/1980 | Slinkard et al. . |
| 4,257,921 | 3/1981 | Slinkard et al. . |
| 4,328,365 * | 5/1982 | Slinkard et al. . |
| 4,448,897 | 5/1984 | Gastinger . |
| 5,750,777 * | 5/1998 | Aubry et al. . |

FOREIGN PATENT DOCUMENTS

| | | |
|---|---|---|
| 1279011 | 7/1969 | (DE) . |
| 2026744 | 4/1971 | (DE) . |
| 2016681 | 10/1971 | (DE) . |
| 2110876 | 10/1971 | (DE) . |
| 2041073 | 2/1972 | (DE) . |
| 2235103 | 2/1974 | (DE) . |
| 2354425 | 5/1975 | (DE) . |
| 3813312 | 11/1989 | (DE) . |
| 19649426 | 6/1998 | (DE) . |
| 1165442 | 10/1969 | (GB) . |
| 1333306 | 10/1973 | (GB) . |
| 1 446 323 * | 4/1976 | (GB) . |

OTHER PUBLICATIONS

Derwent Abstract (#1998–313425[28]) Corresponding to DE 196 49 426.
Derwent Abstract (#1989–325318[45]) Corresponding to DE 3813312.
Derwent Abstract (#71–674715[42]) Corresponding to DE 2016681.
Derwent Abstract (#74–11613v[07]) Corresponding to DE 2235103.
English Abstract Corresponding to DE 2041 073.
English Abstract Corresponding to DE 196 49 426.
Kirk–Othmer encyclopedia of Chemical Technology, Ed. 3, vol. 1, 1978, Wiley & Sons, New York, US.

* cited by examiner

Primary Examiner—Paul J. Killos
Assistant Examiner—Robert W. Deemie
(74) Attorney, Agent, or Firm—Collard & Roe, P.C.

(57) ABSTRACT

A process for preparing acetic acid by gas-phase oxidation of saturated $C_4$-hydrocarbons and their mixtures with unsaturated $C_4$-hydrocarbons in a tube reactor using a coated catalyst comprising an inert nonporous support body and a catalytically active mixed oxide composition comprising (a) one or more oxides selected from the group consisting of titanium dioxide, zirconium dioxide, tin dioxide and aluminum oxide and (b) from 0.1% to 1.5% by weight, based on the weight of the component (a) and per $m^2/g$ of specific surface area of the component (a), of vanadium pentoxide applied to the outer surface of the support body, wherein a gas mixture comprising oxygen or oxygen-containing gas, one or more $C_4$-hydrocarbons and water vapor and having a $C_4$-hydrocarbon/air (oxygen) volume ratio of from 0.2/99.8 to 25/75 and a $C_4$-hydrocarbon/water vapor volume ratio of from 1/1 to 1/60 is reacted over the coated catalyst at a temperature of from 100° C. to 400° C. and a gauge pressure of from 0.2 to 50 bar.

7 Claims, No Drawings

PROCESS FOR PREPARING ACETIC ACID BY GAS-PHASE OXIDATION OF SATURATED C4-HYDROCARBONS AND THEIR MIXTURES WITH UNSATURATED C4-HYDROCARBONS

BACKGROUND OF THE INVENTION

1. Field of the Invention

The present invention relates to a process for preparing acetic acid by gas-phase oxidation of saturated $C_4$-hydrocarbons and their mixtures with unsaturated $C_4$-hydrocarbons using a coated catalyst, and also to a coated catalyst for preparing acetic acid by gas-phase oxidation of saturated $C_4$-hydrocarbons and their mixtures with unsaturated $C_4$- hydrocarbons.

2. The Prior Art

It is known that acetic acid can be prepared by gas-phase oxidation of $C_2$-, $C_3$- and $C_4$-molecules with the aid of a catalyst. However, no process which is fully satisfactory from economic and process engineering points of view has yet been found.

DE-B 1,279,011 describes a process for preparing acetic acid by catalytical gas-phase oxidation of butene by oxygen using catalysts comprising aluminum vanadate and titanium vanadate. These catalysts are prepared by precipitation of the mixed oxides from the corresponding solutions and the mixed oxides can, if desired, be mixed with inert materials such as silica. The catalyst is used in fluidized-bed reactors as a finely divided powder. A disadvantage of such catalysts is the high degree of total oxidation.

To improve the yield obtained by means of such catalysts, DE-A 2,016,681 proposes that the catalysts be pretreated with an oxidizing agent before calcination.

DE-A 2,354,425 (U.S. Pat. No. 3,954,857) proposes treating the calcined titanium-vanadium mixed catalyst with hydrochloric acid to improve the selectivity. The catalysts are used as fully active catalysts, if desired in admixture with inert support materials such as silica.

A further way known from the prior art of improving the activity of titanium-vanadium mixed catalysts in the gas-phase oxidation of butenes to acetic acid is the use of $TiO_2$ in a defined crystal form or with a defined surface area.

DE-A 2,026,744 (U.S. Pat. No. 3,917,682) describes Ti-V mixed catalysts whose $TiO_2$ component is predominantly in the form of rutile. The catalysts can be used in powder form or after being pressed to form shaped bodies.

U.S. Pat. No. 4,448,897 discloses Ti-V catalysts for butene oxidation which comprise $TiO_2$ having a BET surface area of more than 40 $m^2/g$. The catalysts are likewise used in powder form or as compacts.

It is also known from the prior art that the selectivity of Ti-V catalysts in the oxidation of butene can be improved by completely or partly replacing the titanium dioxide by other metal oxides.

For example, DE-A 2,110,876 (GB-A 1,333,306) describes catalysts comprising oxides of molybdenum, tin and vanadium as active components. The catalysts are used in powder form and the mixed oxide catalyst can also, if desired, be applied to finely divided support materials such as silicon dioxide.

U.S. Pat. No. 4,146,734 discloses the use of vanadium mixed oxides which are doped with cerium and further transition metal oxides. The catalyst is used as finely divided powder, but can also be applied as precipitate to finely divided, inert supports.

DE-A 2,235,103 discloses Ti-V mixed oxide catalysts for the gas-phase oxidation of butenes in the form of supported catalysts in which a preformed porous support is impregnated with the mixed solution of the catalyst components.

In all these processes, use is made of catalysts in which the active components are employed as such as powder or compacts. Also the active components can be employed in the form of powder or compacts in which they are diluted with finely divided support materials. For the purposes of the present invention, bulk catalysts also include porous supports which have been impregnated right through with active component as described in DE-A 2,235,103. Also, in this case too, the entire catalyst volume is catalytically active. Disadvantages of fully active catalysts are the high degree of total oxidation and the difficulty of controlling the oxidation reaction at high conversions.

SUMMARY OF THE INVENTION

It is an object of the present invention to provide a process and a catalyst for preparing acetic acid by gas-phase oxidation of saturated $C_4$-hydrocarbons and their mixtures with unsaturated $C_4$-hydrocarbons, which process and catalyst lead to a better yield and a better operating behavior in the oxidation reaction.

The present invention achieves this object and provides a process for preparing acetic acid by gas-phase oxidation of saturated $C_4$-hydrocarbons and their mixtures with unsaturated $C_4$-hydrocarbons in a tube reactor using a coated catalyst comprising an inert nonporous support body and a catalytically active mixed oxide composition comprising (a) one or more oxides selected from the group consisting of titanium dioxide, zirconium dioxide, tin dioxide and aluminum oxide and (b) from 0.1% to 1.5% by weight, based on the weight of the component (a) and per $m^2/g$ of specific surface area of the component (a), of vanadium pentoxide applied to the outer surface of the support body, wherein a gas mixture comprising oxygen or oxygen-containing gas, one or more $C_4$-hydrocarbons and water vapor and having a $C_4$- hydrocarbon/air (oxygen) volume ratio of from 0.2/99.8 to 25/75 and a $C_4$-hydrocarbon/water vapor volume ratio of from 1/1 to 1/60 is reacted over the coated catalyst at a temperature of from 100° C. to 400° C. and a gauge pressure of from 0.2 to 50 bar.

In the process of the present invention, a gas mixture comprising oxygen or an oxygen-containing gas, preferably air, one or more $C_4$-hydrocarbons, preferably butane and its mixtures with butene, water vapor and, if desired, an inert gas is reacted over the coated catalyst at an elevated temperature.

The gas-phase oxidation is carried out in cooled tube reactors which are charged with the coated catalyst and through which the reaction mixture flows. Customary fixed-bed reactors are upright multitube reactors having tube lengths of from 1 m to 10 m, an internal tube diameter of from 10 to 35 mm and a wall thickness of from 1 to 4 mm.

Heat-exchange media which are suitable for cooling are, in particular, water, heat transfer oils and eutectic salt melts, for example mixtures of $KNO_3/NaNO_2$.

The reaction tubes can, if desired, be charged with coated catalysts having different shapes and dimensions and also different compositions of the active components or shells (coatings). In such a case, the coated catalysts can be introduced into the reaction tubes as a random mixture or in zones.

Suitable starting materials are saturated and/or unsaturated hydrocarbons having four carbon atoms or gas mixtures comprising hydrocarbons having four carbon atoms. Unbranched $C_4$-hydrocarbons give higher yields than branched $C_4$-hydrocarbons and butadienes. Particular preference is given to n-butane, 1-butene, 2-butenes and mixtures thereof.

An advantage of the process of the invention for the gas-phase oxidation of $C_4$-hydrocarbons using the coated catalyst is that it is also possible to use gas mixtures comprising compounds which do not react to form acetic acid or react in this way only to a small extent or in poor yields. Thus, it is also possible to use cheap raw material mixtures from refineries, for example "$C_4$ fraction" (predominantly butadiene and i-butene), "raffinate 1" (predominantly i-butene), "raffinate 2" (predominantly 1-butene and 2-butenes) and mixtures which comprise not only $C_4$-hydrocarbons but also linear and/or branched and/or cyclic hydrocarbons having more or less than four carbon atoms. Examples of these hydrocarbons include methane, ethane, ethene, propene, propane, pentanes, pentenes, pentadienes, cyclopentane, cyclopentene, cyclopentadiene, methylcyclopentane, etc., as starting material. Likewise, alcohols, aldehydes, ethers, ketones and esters having 1–8 carbon atoms may also be present. The raw material mixtures mentioned can, if appropriate, also be subjected to a hydrogenation or purification step before use.

The reaction temperature for the oxidation of the butane and/or butene/oxygen (air)/water vapor reaction mixtures is generally from 100° C. to 400° C., preferably from 150° C. to 300° C.

The reaction can be carried out at the banking-up pressure resulting from flow through the catalyst bed or under elevated pressure. Preference is given to working at a gauge pressure of from 0.2 to 50 bar, particularly preferably from 1 to 16 bar.

The $C_4$-hydrocarbon/air (oxygen) volume ratio is generally from 0.2/99.8 to 25/75, preferably 1/99 to 5/95. The $C_4$-hydrocarbon/water vapor volume ratio is generally from 1/1 to 1/60, preferably from 1/5 to 1/25. The space velocity of the gas mixture in the reactor is from 400 to 10000 $h^{-1}$, preferably from 600 to 6000 $h^{-1}$ (STP).

After the reaction, the acetic acid formed is separated off by cooling and precipitation or by absorption in a suitable solvent. The acetic acid which has been separated off is purified further by suitable methods, for example distillation or extraction. The tailgas can be recirculated.

As a further embodiment of the present invention, particularly suitable coated catalysts for preparing acetic acid by gas-phase oxidation of saturated hydrocarbons having four carbon atoms and their mixtures with unsaturated hydrocarbons having four carbon atoms are as follows. These catalysts are the ones in which the active composition is applied as a thin layer on a nonporous support body.

The coated catalysts of the present invention comprise an inert nonporous support body and an effective catalytic amount of a catalytically active mixed oxide composition comprising (a) one or more oxides selected from the group consisting of titanium dioxide, zirconium dioxide, tin dioxide, aluminum oxide and (b) from 0.1% to 1.5% by weight, based on the weight of the component (a) and per $m^2/g$ of specific surface area of the component (a), of vanadium pentoxide applied to the outer surface of the support body.

The provision "% by weight based on the weight of the component (a) and per $m^2/g$ of specific surface area of the component (a)" means that the proportion by weight of component (b) to be used is dependent on the specific surface area of the component (a). Thus, for example, at a specific surface area of the component (a) of 10 $m^2/g$, the proportion of component (b) is from 1% to 15% by weight, based on the weight of the component (a).

$TiO_2$ can be used either in the rutile form or in the anatase form or as a mixture thereof. Titanium dioxide having a BET surface area of from 20 to 400 $m^2/g$, preferably from 40 to 300 $m^2/g$, is preferably used as component (a). If mixtures of titanium dioxide with aluminum oxide, zirconium dioxide or tin dioxide are used, from 5% to 95% by weight, preferably from 5% to 50% by weight, of the titanium dioxide can be replaced by zirconium dioxide, aluminum oxide or tin dioxide.

As an additional component (a), it is possible for one or more oxides selected from the group consisting of the oxides of boron, silicon, hafnium, niobium, tungsten, lanthanum and cerium to be present. When the component (a) is doped with the abovementioned oxides, the latter are generally present in an amount of from 1% to 30% by weight, based on the total weight of the component (a).

The proportion of component (b) is preferably from 0.1% to 1% by weight, particularly preferably from 0.1% to 0.5% by weight, in each case based on the weight of the component (a) and per $m^2/g$ of specific surface area of the component (a).

In the component (b), part of the vanadium pentoxide, preferably from 10% to 90% by weight, may, if desired, be replaced by one or more oxides of molybdenum, chromium and antimony. If desired, one or more oxides of alkali metals, elements of main groups V and VI of the Periodic Table of the Elements and the transition metals may be present as additional component (b). Examples are the oxides of lithium, sodium, potassium, rubidium, cesium, phosphorus, bismuth, sulfur, selenium, tellurium, manganese, iron, cobalt, palladium, copper, silver, gold, zinc and cadmium. In general, the amount of these dopants is from 0.005% to 15% by weight, calculated as oxides and based on the total weight of the component (b). The proportion of alkali metal oxides and noble metal oxides is preferably from 0.005% to 1.0% by weight.

Preference is given to compositions comprising a component (a) which has a high surface area of from 40 to 300 $m^2/g$ and in which tin oxide or tungsten oxide may additionally be present and a component (b) which is doped with Mo, Cr, Sb and/or Au.

The catalytically active mixed oxide composition may, if desired, further comprise from 10% to 50% by weight, based on the total weight of the catalytically active mixed oxide composition, of inert diluents such as silicon dioxide, silicon carbide or graphite.

The catalytically active mixed oxide composition is applied in a proportion of from 1% to 40% by weight, preferably from 5% to 25% by weight, in each case based on the total weight of support body and active composition, as a shell to the outer surface of the support body. The thickness of the layer is generally from 10 to 2000 $\mu$m, preferably from 100 to 1000 $\mu$m. The coated catalyst can also have a plurality of active layers which differ in their composition. It is also possible for one or more constituents of the active components (a) and (b) to be present in different concentrations in the individual layers.

In general, the catalytically active mixed oxide composition is applied in one layer. To influence the catalyst activity and to improve the adhesion to the support body, it is also possible for two or more layers to be applied.

Preferred embodiments having a plurality of layers are those in which the inner layer comprises only component (a)

and the outer layer comprises the components (a) and (b). Other preferred multilayer embodiments are those in which the inner and outer layers each comprise the components (a) and (b) but the component (a) in the inner layer has a higher specific surface area than the component (a) in the outer layer.

Suitable materials for the inert, nonporous support body are all nonporous materials which are inert under the operating conditions of the gas-phase oxidation and are stable over the period of operation. Examples are steatite, Duranit, silicon carbide, magnesium oxide, silicon oxide, silicates, aluminates, metals such as stainless steel and also, if desired, mixtures of these materials. Preference is given to ceramic material such as steatite.

The support body is nonporous, by which it is meant that the BET surface area of the support body is <1 m²/g and the porosity is <0.1, where $$\text{porosity}=[1-(\text{density}_{shaped\ body}/\text{density}_{substance})].$$

The inert, nonporous support body can have any desired shape. Examples of suitable shapes are spheres, cylinders, cuboids, tori, saddles, spindles, helices. The basic shapes can also have one or more recesses such as depressions, grooves, holes, or projecting parts such as studs, points, ribs. Further examples are rings, ring segments, ribbed rings, spheres with holes through the middle, sphere segments. Likewise suitable as supports are ordered packings such as monoliths or cross-channel structures. Preference is given to support shapes having as high as possible a geometric surface area per unit volume, for example rings.

The dimensions of the support bodies are determined by the reactors for the gas-phase oxidation. The shaped bodies generally have a length or a diameter of from 2 to 20 mm. The wall thickness, for example in the case of rings or hollow cylinders, is advantageously from 0.1 to 4 mm.

To produce the coated catalysts, the catalytically active mixed oxide composition is applied to the support body in a known manner, for example by coating the supports in a rotary furnace with an aqueous slurry or in a coating drum. It is advantageous to provide the premix of the active composition with a binder which remains in the active layer after application to improve the layer's mechanical stability. It is particularly advantageous to mix the aqueous suspension of the active components with an aqueous copolymer dispersion, preferably of vinyl acetate/vinyl laurate, in an amount of from 5% to 40% by weight, based on the solids content of the dispersion and on the sum of the dry weights of active composition and dispersion. Then this mixture is applied to the inert, nonporous support bodies in a spray-drying step.

Repeating this step using further spray suspensions of a different composition enables catalysts having a layer-like structure of the active catalyst shell to be produced. If one or more components of the active composition are introduced in amounts which alter over time during the application process, catalytically active layers which display a steady change in composition in the radial direction are obtained.

DETAILED DESCRIPTION OF PREFERRED EMBODIMENTS

Other objects and features of the present invention will become apparent from the following examples. It should be understood, however, that the examples are designed for the purpose of illustration only and not as a definition of the limits of the invention.

The catalysts in the examples were produced by milling the amounts of active components indicated in the examples together with water, and subsequently adding a copolymer dispersion of vinyl acetate and vinyl laurate having a solids content of 50% by weight. Then the finished suspension was applied by spraying, with evaporation of the water, to 1000 g of steatite spheres (4 mm diameter, Examples 1–29) or to 1200 g of steatite rings having dimensions of 7×4×4 mm (Examples 30–31) (BET surface area <0.01, porosity <0.01).

To test their performance, the catalysts from Examples 3 to 32 and Comparative Examples 1 and 2 were introduced into a reaction tube having an internal diameter of 12.5 mm. The tube was externally cooled by means of a salt melt subjected to forced circulation. Unless otherwise indicated, all reactions were carried out at a gauge pressure of $1\times10^5$ Pa.

The amounts of catalyst indicated in the examples were introduced into the reactor (fill height of 1400 mm). Unless otherwise indicated in the examples, the catalyst was heated for 6 hours at 410° C. under an air flow of 220 standard 1/h in the reaction tube prior to operation. The reaction gas consisted, unless otherwise indicated, of 80 standard 1/h of air, 0.81 standard 1/h of 1-butene and 16.2 standard 1/h of water vapor.

The selectivity [in mol %] was calculated as follows: acetic acid selectivity based on total $C_4$ conversion (mol %)=(((mol/h of acetic acid in the crude acid)/2)/(mol/h of butene reacted +mol/h of butane reacted))*100 Formic acid selectivity based on total $C_4$ conversion (mol %)=(((mol/h of formic acid in the crude acid)/4)/(mol/h of butene reacted +mol/h of butane reacted))*100

The yield was determined using the following equation: acetic acid yield [% by weight]=[(kg of acetic acid separated out/kg of starting material used)×100]

The catalyst compositions and the test conditions and test results are summarized in Table 1.

EXAMPLE 1

(Oxidation of Butane to Acetic Acid)

A circulation reactor comprising a reaction tube having a length of 6 m and an internal diameter of 19 mm was charged with a catalyst comprising 163 g of $TiO_2$ (BET surface area: 75 m²/g), 29 g of $Sb_2O_3$, 16 g of $V_2O_5$ and 23 g of graphite on steatite rings having dimensions of 7×4×4 mm. The fill height was 6000 mm. The tube was externally cooled by means of an oil bath subjected to forced circulation. The catalyst was heated for 6 hours at 250° C. under an air flow of 250 standard 1/h in the reaction tube before operation. The reaction conditions were selected such that a temperature of 205° C. and a pressure of 10 bar (gauge pressure) prevailed in the reactor. The composition of the feed was 120 g/h of n-butane, 136 g/h of oxygen and 700 g/h of water vapor. The circulation was set such that a circulating gas flow of 20 kg/h was obtained. The butane conversion was 53% and the oxygen conversion was 96%. The acetic acid selectivity was 65 mol % and the formic acid selectivity was 5 mol %.

EXAMPLE 2

(Oxidation of a Mixture of n-butane and 1-butene to Acetic Acid)

A circulation reactor comprising a reaction tube having a length of 6 m and an internal diameter of 19 mm was charged with a catalyst comprising 163 g of $TiO_2$ (BET surface area: 75 m²/g), 29 g of $Sb_2O_3$, 16 g of $V_2O_5$ and 23 g of graphite on steatite rings having dimensions of 7×4×4 mm. The fill height was 6000 mm. The tube was externally cooled by means of an oil bath subjected to forced circulation. The catalyst was heated for 6 hours at 250° C. under an air flow of 250 standard 1/h in the reaction tube before operation. The reaction conditions were selected such that a temperature of 200° C. and a pressure of 10 bar (gauge pressure) prevailed in the reactor. The composition of the feed was 120 g/h of 1-butene, 80 g/h of n-butane, 311 g/h of oxygen and 700 g/h of water vapor. The circulation was set such that a circulating gas flow of 20 kg/h was obtained. The butene conversion was 99%, the butane conversion was 53% and the oxygen conversion was 96%. The acetic acid selectivity was 64 mol % and the formic acid selectivity was 6 mol %.

EXAMPLE 3
(Two-layer Coated Catalyst)

To prepare the first spraying suspension, 70.42 g of titanium dioxide (>70% anatase modification) having a BET surface area of 48 $m^2/g$, 7.43 g of titanium dioxide (100% anatase modification, BET: 8 $m^2/g$), 14.67 g of $V_2O_5$ and 900 ml of deionized water were milled for 20 hours in a ball mill. 29 g of a copolymer dispersion of vinyl acetate and vinyl laurate having a solids content of 50% by weight were then added to the homogeneous suspension and the mixture was intimately mixed by stirring. To prepare the second spraying suspension, 5 g of titanium dioxide (100% anatase modification, BET: 8 $m^2/g$), 3 g of a copolymer dispersion of vinyl acetate/vinyl laurate having a solids content of 50% by weight and 100 ml of deionized water were intimately mixed by stirring. The second spraying suspension was first applied to 1000 g of 4 mm steatite spheres and dried. The first spraying suspension was then applied and dried. 202 g of the catalyst were introduced into the reactor (fill height of 1400 mm). At a salt bath temperature of 213.5° C., a conversion of 88.6% was achieved and the acetic acid yield was 116.25% by weight.

EXAMPLE 4
(Single-layer Coated Catalyst, Low Surface Area)

211 g of titanium dioxide (>70% anatase modification) having a BET surface area of 48 $m^2/g$ were milled together with 44 g of $V_2O_5$ and 1500 ml of deionized water for 20 hours in a ball mill and, after addition of the binder, applied to the steatite spheres. 200 g of catalyst were introduced into the reactor (fill height of 1400 mm). At a salt bath temperature of 198° C., a conversion of 88% was achieved and the acetic acid yield was 116.5% by weight.

EXAMPLE 5
(High Proportion of Water Vapor)

The procedure of Example 2 was repeated using a reaction gas comprising 100 standard 1/h of air, 1.01 standard 1/h of 1-butene and 50.5 standard 1/h of water vapor. At a salt bath temperature of 197° C., a conversion of 75% was achieved and the acetic acid yield was 103% by weight.

EXAMPLE 6
(High Layer Thickness)

297.1 g of titanium dioxide (>70% anatase modification) having a BET surface area of 48 $m^2/g$ were milled together with 51.3 g of $V_2O_5$ and 1500 ml of deionized water for 19 hours in a ball mill and, after addition of the binder, applied to the steatite spheres. 177 g of catalyst were introduced into the reactor (fill height of 1400 mm). The reaction gas comprised 24.8 standard 1/h of water vapor. At a salt bath temperature of 196° C., a conversion of 95% was achieved and the acetic acid yield was 113.5% by weight.

EXAMPLE 7
(High Vanadium Content)

135 g of titanium dioxide (anatase modification) having a BET surface area of 75 $m^2/g$ were milled together with 120 g of $V_2O_5$ and 1400 ml of deionized water for 24 hours in a ball mill and, after addition of the binder, applied to the steatite spheres. 168 g of catalyst were introduced into the reactor (fill height of 1400 mm). The reaction gas comprised 24.8 standard 1/h of water vapor. At a salt bath temperature of 189° C., a conversion of 92% was achieved and the acetic acid yield was 105% by weight.

EXAMPLE 8
(Tungsten Doping)

186.2 g of titanium dioxide (anatase modification containing 10% by weight of $WO_3$) having a BET surface area of 75 $m^2/g$ were milled together with 68.9 g of $V_2O_5$ and 700 ml of deionized water for 120 hours in a ball mill and, after addition of the binder, applied to the steatite spheres. 192 g of catalyst were introduced into the reactor (fill height of 1400 mm). At a salt bath temperature of 179° C., a conversion of 95% was achieved, the hot spot temperature was 190° C. and the acetic acid yield was 116.2% by weight.

EXAMPLE 9
(Low $C_4$ Concentration)

The procedure of Example 5 was repeated using a reaction gas comprising 206 standard 1/h of air, 0.62 standard 1/h of 1-butene and 42 standard 1/h of water vapor. At a salt bath temperature of 192.5° C., a conversion of 96% was achieved and the acetic acid yield was 128.1% by weight.

EXAMPLE 10
(Sinqle-layer Coated Catalyst, Very High Surface Area)

186.37 g of titanium dioxide (anatase modification) having a BET surface area of 250 $m^2/g$ were milled together with 68 g of $V_2O_5$ and 1500 ml of deionized water for 18 hours in a ball mill and, after addition of the binder, applied to the steatite spheres. 153.4 g of catalyst were introduced into the reactor (fill height of 1400 mm). At a salt bath temperature of 174° C., a conversion of 96.2% was achieved and the acetic acid yield was 133% by weight.

EXAMPLE 11
(Cesium/phosphorus Doping)

217.5 g of titanium dioxide (>70% anatase modification) having a BET surface area of 48 $m^2/g$ were milled together with 37.6 g of $V_2O_5$, 1.6 g of cesium carbonate, 4.8 g of ammonium dihydrogen phosphate and 1000 ml. of deionized water for 48 hours in a ball mill and, after addition of the binder, applied to the steatite spheres. 166.8 g of catalyst were introduced into the reactor (fill height of 1400 mm). At a salt bath temperature of 221.5° C., a conversion of 94% was achieved, the hot spot temperature was 223° C. and the acetic acid yield was 105.5% by weight.

EXAMPLE 12
(Molybdenum Doing)

219.98 g of titanium dioxide (anatase modification) having a BET surface area of 44.4 $m^2/g$ were milled together with 31.33 g of $V_2O_5$, 6.25 g of molybdenum trioxide and 1000 ml of deionized water for 22 hours in a ball mill and, after addition of the binder, applied to the steatite spheres. 167 g of catalyst were introduced into the reactor (fill height of 1400 mm). At a salt bath temperature of 194° C., a conversion of 93% was achieved and the acetic acid yield was 112.4% by weight.

EXAMPLE 13
(Two-layer Coated Catalyst)

First spray suspension: 101.65 g of titanium dioxide (100% anatase modification) having a BET surface area of 75 $m^2/g$ were milled together with 27.1 g of $V_2O_5$ and 500 ml of deionized water for 20 hours in a ball mill. 43.50 g of a copolymer dispersion of vinyl acetate and vinyl laurate having a solids content of 50% by weight were then added to the homogeneous suspension and the mixture was intimately mixed by stirring.

Second spray suspension: 122.6 g of titanium dioxide (100% anatase modification, BET: 17 $m^2/g$), 7.50 g of vanadium pentoxide and 500 ml of deionized water were milled for 20 hours in a ball mill. 43.49 g of a copolymer dispersion of vinyl acetate and vinyl laurate having a solids content of 50% by weight were then added to the homogeneous suspension and the mixture was intimately mixed by stirring.

The first spray suspension was applied first to 1000 g of 4 mm steatite spheres. The second spray suspension was then applied. 167 g of catalyst were introduced into the reactor (fill height of 1400 mm). At a salt bath temperature of 185° C., a conversion of 92% was achieved and the acetic acid yield was 116% by weight.

EXAMPLE 14
(Mo/Na Doping)

100.0 g of titanium dioxide (100% anatase modification) having a BET surface area of 15 $m^2/g$ were milled together with 5.32 g of $V_2O_5$, 1.065 g of molybdenum trioxide, 0.245 g of sodium carbonate and 1000 ml of deionized water for 20 hours in a ball mill and, after addition of the binder, applied to the steatite spheres. 202 g of catalyst were introduced into the reactor (fill height of 1400 mm). At a salt bath temperature of 252° C., a conversion of 92% was achieved and the acetic acid yield was 96.4% by weight.

EXAMPLE 15
(Low Vanadium Content)

225 g of titanium dioxide (100% anatase modification) having a BET surface area of 75 $m^2/g$ were milled together with 30 g of $V_2O_5$ and 1500 ml of deionized water for 35 hours in a ball mill and, after addition of the binder, applied to 1000 g of 4 mm steatite spheres. 158 g of catalyst were introduced into the reactor (fill height of 1400 mm). At a salt bath temperature of 179° C., a conversion of 95% was achieved and the acetic acid yield was 121.3%.

EXAMPLE 16
(Sulfur Doping)

188 g of titanium dioxide (anatase modification) having a BET surface area of 140 $m^2/g$ and a sulfate content of 4.6% by weight were milled together with 69 g of $V_2O_5$ and 1500 ml of deionized water for 100 hours in a ball mill and, after addition of the binder, applied to the steatite spheres. 161 g of catalyst were introduced into the reactor (fill height of 1400 mm). At a salt bath temperature of 172.5° C., a conversion of 95% was achieved and the acetic acid yield was 130% by weight.

EXAMPLE 17
(High Mo Content)

225 g of titanium dioxide (anatase modification) having a BET surface area of 75 $m^2/g$ were milled together with 10 g of $V_2O_5$, 20 g of $MoO_3$ and 1500 ml of deionized water for 68 hours in a ball mill and, after addition of the binder, applied to the steatite spheres. 162 g of catalyst were introduced into the reactor (fill height of 1400 mm). At a salt bath temperature of 183.5° C., a conversion of 94.5% was achieved and the acetic acid yield was 120% by weight.

EXAMPLE 18
(Antimony Doping)

225 g of titanium dioxide (anatase modification) having a BET surface area of 75 $m^2/g$ were milled together with 26.3 g of $V_2O_5$, 10.5 g of $Sb_2O3$ and 2000 ml of deionized water for 24 hours in a ball mill and, after addition of the binder, applied to the steatite spheres. 166 g of catalyst were introduced into the reactor (fill height of 1400 mm). At a salt bath temperature of 175° C., a conversion of 94.4% was achieved and the acetic acid yield was 142% by weight.

EXAMPLE 19
(Mo/Sb Doping)

225 g of a titanium dioxide having a BET surface area of 75 $m^2/g$ were milled together with 20 g of $V_2O_5$, 5 g of $MoO_3$, 12 g of $Sb_2O_3$ and 1500 ml of deionized water for 14 hours in a ball mill and, after addition of the binder, applied to 1000 g of steatite spheres. 166.2 g of catalyst were introduced into the reactor (fill height of 1400 mm). At a salt bath temperature of 178° C., a conversion of 96% was achieved and the acetic acid yield was 125.2% by weight.

EXAMPLE 20
(Sb Doping)

225 g of a titanium dioxide having a BET surface area of 75 $m^2/g$ were milled together with 22 g of $V_2O_5$, 40 g of $Sb_2O_3$ and 1500 ml of deionized water for 14 hours in a ball mill and, after addition of the binder, applied to 1000 g of steatite spheres. 165.0 g of catalyst were introduced into the reactor (fill height of 1400 mm). At a salt bath temperature of 172° C., a conversion of 94% was achieved and the acetic acid yield was 131.6% by weight.

EXAMPLE 21
(Bismuth Dosing)

225 g of titanium dioxide (100% anatase modification) having a BET surface area of 75 $m^2/g$ were milled together with 26.3 g of $V_2O_5$, 10.5 g of $Bi_2O_3$ and 1500 ml of deionized water for 48 hours in a ball mill and, after addition of the binder, applied to the steatite spheres. 151 g of catalyst were introduced into the reactor (fill height of 1400 mm). At a salt bath temperature of 179° C., a conversion of 90.2% was achieved and the acetic acid yield was 120% by weight.

EXAMPLE 22
(Tellurium Doping)

225 g of titanium dioxide (100% anatase modification) having a BET surface area of 75 $m^2/g$ were milled together with 26.3 g of $V_2O_5$, 10.5 g of $TeO2$ and 2000 ml of deionized water for 47 hours in a ball mill and, after addition of the binder, applied to the steatite spheres. 159 g of catalyst were introduced into the reactor (fill height of 1400 mm). At a salt bath temperature of 203° C., a conversion of 88% was achieved and the acetic acid yield was 103% by weight.

EXAMPLE 23
(Manganese Doping)

225 g of titanium dioxide (100% anatase modification) having a BET surface area of 75 $m^2/g$ were milled together with 26.3 g of $V_2O_5$, 10.5 g of $MnO_2$ and 1500 ml of deionized water for 19 hours in a ball mill and, after addition of the binder, applied to the steatite spheres. 158 g of catalyst were introduced into the reactor (fill height of 1400 mm). At a salt bath temperature of 194° C., a conversion of 90% was achieved and the acetic acid yield was 111.3% by weight.

EXAMPLE 24

(Copper Doping)

225 g of titanium dioxide (100% anatase modification) having a BET surface area of 75 m$^2$/g were milled together with 26.3 g of V$_2$O$_5$, 1.42 g of Cu(NO$_3$)$_2$·3H$_2$O and 1200 ml of deionized water for 19 hours in a ball mill and, after addition of the binder, applied to the steatite spheres. 159 g of catalyst were introduced into the reactor (fill height of 1400 mm). At a salt bath temperature of 180° C., a conversion of 94% was achieved and the acetic acid yield was 120% by weight.

EXAMPLE 25

(Zinc Doping)

225 g of titanium dioxide (100% anatase modification) having a BET surface area of 75 m$^2$/g were milled together with 26.3 g of V$_2$O$_5$, 1.11 g of zinc(II) acetate dihydrate and 1500 ml of deionized water for 43 hours in a ball mill and, after addition of the binder, applied to the steatite spheres. 157 g of catalyst were introduced into the reactor (fill height of 1400 mm). At a salt bath temperature of 178.5° C., a conversion of 94.6% was achieved and the acetic acid yield was 124.2% by weight.

EXAMPLE 26

(Gold Doping)

225 g of titanium dioxide (100% anatase modification) having a BET surface area of 75 m$^2$/g were milled together with 26.3 g of V$_2$O$_5$, 0.94 g of tetrachloroauric acid and 1500 ml of deionized water for 46 hours in a ball mill and, after addition of the binder, applied to the steatite spheres. 162 g of catalyst were introduced into the reactor (fill height of 1400 mm). At a salt bath temperature of 182° C., a conversion of 95.8% was achieved and the acetic acid yield was 128.4% by weight.

EXAMPLE 27

(Chromium Doping)

225 g of titanium dioxide (100% anatase modification) having a BET surface area of 75 m$^2$/g were milled together with 24 g of V$_2$O$_5$, 2.9 g of chromium trioxide and 1500 ml of deionized water for 22 hours in a ball mill and, after addition of the binder, applied to the steatite spheres. 174.8 g of catalyst were introduced into the reactor (fill height of 1400 mm). At a salt bath temperature of 184° C., a conversion of 95% was achieved and the acetic acid yield was 128% by weight.

EXAMPLE 28

(Ti/Sn Catalyst)

200 g of titanium dioxide (100% anatase modification) having a BET surface area of 75 m$^2$/g were milled together with 70 g of tin tetrachloride pentahydrate, 26.3 g of V$_2$O$_5$ and 1500 ml of deionized water for 46 hours in a ball mill and, after addition of the binder, applied to the steatite spheres. 160.1 g of catalyst were introduced into the reactor (fill height of 1400 mm). At a salt bath temperature of 191° C., a conversion of 94% was achieved and the acetic acid yield was 130% by weight.

EXAMPLE 29

(Ti/Zr Catalyst)

171 g of a Ti/Zr mixed oxide (9% by weight of ZrO$_2$) prepared by a sol-gel method and having a BET surface area of 75 m$^2$/g were milled together with 15.2 g of V$_2$O$_5$, 3.8 g of MoO3, 9.1 g of Sb$_2$O3 and 1000 ml of deionized water for 14 hours in a ball mill and, after addition of the binder, applied to 760 g of the steatite spheres. 162.4 g of catalyst were introduced into the reactor (fill height of 1400 mm). At a salt bath temperature of 201° C., a conversion of 93% was achieved and the acetic acid yield was 112% by weight.

EXAMPLE 30

(Ti/Zr Catalyst)

171 g of a Ti/Zr mixed oxide (9% by weight of ZrO$_2$) prepared by a sol-gel method and having a BET surface area of 110 m$^2$/g were milled together with 36.8 g of V$_2$O$_5$, 9.2 g of MoO$_3$, 21.3 g of Sb$_2$O$_3$ and 1000 ml of deionized water for 14 hours in a ball mill and, after addition of the binder, applied to 760 g of the steatite spheres. 155.5 g of catalyst were introduced into the reactor (fill height of 1400 mm). At a salt bath temperature of 199° C., a conversion of 95% was achieved and the acetic acid yield was 115% by weight.

EXAMPLE 31

(Niobium Dopinq)

151 g of a Ti/Nb mixed oxide (9% by weight of Nb$_2$O$_5$) prepared by a sol-gel method and having a BET surface area of 70 m$^2$/g were milled together with 14.5 g of V$_2$O$_5$, 3.6 g of MoO$_3$, 8.7 g of Sb$_2$O$_3$ and 800 ml of deionized water for 14 hours in a ball mill and, after addition of the binder, applied to 700 g of the steatite spheres. 169.5 g of catalyst were introduced into the reactor (fill height of 1400 mm). At a salt bath temperature of 219° C., a conversion of 96% was achieved and the acetic acid yield was 105% by weight.

EXAMPLE 32

(Ca/Mo/Sb/SO$_4$ Doping)

225 g of a titanium dioxide having a BET surface area of 75 m$^2$/g were milled together with 20 g of V$_2$O$_5$, 5 g of MoO$_3$, 12 g of Sb$_2$O$_3$, 38 g of CaSO$_4$.2H$_2$O and 1500 ml of deionized water for 14 hours in a ball mill and, after addition of the binder, applied to 1000 g of steatite spheres. 158.5 g of catalyst were introduced into the reactor (fill height of 1400 mm). At a salt bath temperature of 181° C., a conversion of 96% was achieved and the acetic acid yield was 120.3% by weight.

COMPARATIVE EXAMPLE 1

(Bulk Catalyst)

200 g of titanium dioxide (100% anatase modification) having a BET surface area of 8 m$^2$/g were mixed with 8.1 g of V$_2$O$_5$ and 10 g of graphite, milled, screened and pressed to form cylindrical pellets (4×4 mm). 155 g of catalyst were introduced into the reactor (fill height of 1400 mm). At a salt bath temperature of 247° C., a conversion of 90% was achieved and the acetic acid yield was 77% by weight.

COMPARATIVE EXAMPLE 2

(In Accordance with DE-A 2,235,103)

A porous (porosity=0.65) alpha-aluminum oxide support (irregular crushed material) was impregnated under reduced pressure with a hydrochloric acid solution of vanadium/ titanium prepared as described for Example Catalyst 1 in DE-A 2235103 and was then dried and calcined as described in that example. 134.5 g of the material screened to 4 mm were introduced into the reactor (fill height: 1400). At a salt bath temperature of 200° C., a butene conversion of 96% was achieved and the acetic acid yield was only 94% by weight. Significant amounts of maleic acid and propionic acid were obtained as by-products.

TABLE 1

| Ex. | Catalyst | Reaction conditions | Temperature [°C.] | Conversion [%] | Yield [%] |
|---|---|---|---|---|---|
| 3 | 2-layer | standard | 213.5 | 86.6 | 116.25 |
| 4 | low surface area | standard | 198.0 | 88.0 | 116.5 |
| 5 | low surface area | high water vapor conc. | 197.0 | 75.0 | 103.0 |
| 6 | thick layer | high water vapor conc. | 196.0 | 95.0 | 113.5 |
| 7 | high V content | high water vapor conc. | 189.0 | 92.0 | 105.0 |
| 8 | W doping | standard | 179.0 | 95.0 | 116.2 |
| 9 | low $C_4$ content | low butene conc. | 192.5 | 96.0 | 128.1 |
| 10 | high surface area | standard | 174.0 | 96.2 | 133.0 |
| 11 | Cs/P doping | standard | 221.5 | 94.0 | 105.5 |
| 12 | Mo doping | standard | 194.0 | 93.0 | 112.4 |
| 13 | 2-layer | standard | 185.0 | 92.0 | 116.0 |
| 14 | Mo/Na doping | standard | 252.0 | 92.0 | 96.4 |
| 15 | low vanadium content | standard | 179.0 | 95.0 | 121.3 |
| 16 | S doping | standard | 172.5 | 95.0 | 130.0 |
| 17 | high Mo content | standard | 183.5 | 94.5 | 120.0 |
| 18 | Sb doping | standard | 175.0 | 94.4 | 142.0 |
| 19 | Mo/Sb doping | standard | 178.0 | 96.0 | 125.2 |
| 20 | Sb doping | standard | 172.0 | 94.0 | 131.6 |
| 21 | Bi doping | standard | 179.0 | 90.2 | 120.0 |
| 22 | Te doping | standard | 203.0 | 88.0 | 103.0 |
| 23 | Mn doping | standard | 194.0 | 90.0 | 111.3 |
| 24 | Cu doping | standard | 180.0 | 94.0 | 120.0 |
| 25 | Zn doping | standard | 178.5 | 94.6 | 124.2 |
| 26 | Au doping | standard | 182.0 | 95.8 | 128.4 |
| 27 | Cr doping | standard | 184.0 | 95.0 | 128.0 |
| 28 | Ti/Sn catalyst | standard | 191.0 | 94.0 | 130.0 |
| 29 | Ti/Zr catalyst | standard | 201.0 | 93.0 | 112.0 |
| 30 | Ti/Zr catalyst | standard | 199.0 | 95.0 | 115.0 |
| 31 | Nb doping | standard | 219.0 | 96.0 | 105.0 |
| 32 | Ca/Mo/Sb/SO4 doping | standard | 181.0 | 96.0 | 120.3 |
| C1 | fully active catalyst | standard | 247.0 | 90.0 | 77.0 |
| C2 | DE-A 2235103 | standard | 200.0 | 96.0 | 94.0 |

Accordingly, while a few embodiments of the present invention have been shown and described, it is to be understood that many changes and modifications may be made thereunto without departing from the spirit and scope of the invention as defined in the appended claims.

What is claimed is:

1. A process for preparing acetic acid by gas-phase oxidation of saturated $C_4$-hydrocarbons and their mixtures with unsaturated $C_4$-hydrocarbons in a tube reactor comprising
  (1) providing in said tube reactor a coated catalyst comprising an inert nonporous support body having an outer surface and a catalytically active mixed oxide composition coating applied to the outer surface of the support body, said mixed oxide composition comprising
    (a) one or more oxides selected from the group consisting of titanium dioxide, zirconium dioxide, tin dioxide and aluminum oxide as component (a) and wherein the coated catalyst further comprises, as component (a), one or more oxides selected from the group consisting of the oxides of boron, silicon, hafnium, niobium, lanthanum and cerium in an amount of from 1 to 30% by weight, based on the total weight of the component (a),
    (b) from 0.1% to 1.5% by weight, based on the weight of the component (a) of vanadium pentoxide as component (b); and
  (2) reacting a gas mixture comprising oxygen or oxygen-containing gas, one or more $C_4$-hydrocarbons selected from the group consisting of a saturated $C_4$-hydrocarbon and a mixture of a saturated $C_4$-hydrocarbon with an unsaturated $C_4$-hydrocarbon and water vapor and having a $C_4$-hydrocarbon/air (oxygen) volume ratio of from 0.2/99.8 to 25/75 and a $C_4$-hydrocarbon/water vapor volume ratio of from 1/1 to 1/60 in contact with the coated catalyst at a temperature of from 100° C. to 400° C. and a gauge pressure of from 0.2 to 50 bar to produce the acetic acid.

2. The process as claimed in claim 1, comprising introducing the coated catalyst into the tube reactor in zones.

3. A process for preparing acetic acid by gas-phase oxidation of saturated $C_4$-hydrocarbons and their mixtures with unsaturated $C_4$-hydrocarbons in a tube reactor comprising
  (1) providing in said tube reactor a coated catalyst comprising an inert nonporous support body having an outer surface and a catalytically active mixed oxide composition coating applied to the outer surface of the support body, said mixed oxide composition comprising
    (a) one or more oxides selected from the group consisting of titanium dioxide, zirconium dioxide, tin dioxide and aluminum oxide as component (a) and wherein the coated catalyst further comprises, as component (a), one or more oxides selected from the group consisting of the oxides of boron, silicon, hafnium, niobium, lanthanum and cerium in an amount of from 1 to 30% by weight, based on the total weight of the component (a),
    (b) from 0.1% to 1.5% by weight, based on the weight of the component (a) of vanadium pentoxide as component (b); and
    replacing in component (b) of the coated catalyst, part of the vanadium pentoxide by one or more additional oxides selected from the group consisting of molybdenum, chromium, antimony, alkali metals, alkaline earth metals, elements of main groups V and VI of the Periodic Table of the Elements and the transition metals as an additional component (b); and
  (2) reacting a gas mixture comprising oxygen or oxygen-containing gas, one or more $C_4$-hydrocarbons selected from the group consisting of a saturated $C_4$-hydrocarbon and a mixture of a saturated $C_4$-hydrocarbon with an unsaturated $C_4$-hydrocarbon and water vapor and having a $C_4$-hydrocarbon/air (oxygen) volume ratio of from 0.2/99.8 to 25/75 and a $C_4$-hydrocarbon/water vapor volume ratio of from 1/1 to 1/60 in contact with the coated catalyst at a temperature of from 100° C. to 400° C. and a gauge pressure of from 0.2 to 50 bar to produce the acetic acid.

4. The process as claimed in claim 1, comprising applying the catalytically active mixed oxide composition in the coated catalyst in an amount of from 1 to 40% by weight, based on the total weight of support body and active composition, as a shell having a thickness of from 10 to 2000 μm on the outer surface of the support body.

5. The process as claimed in claim 1, wherein the coated catalyst comprises one or more layers of catalytically active mixed oxide composition.

6. The process as claimed in claim 1, wherein the coated catalyst comprises a plurality of layers with an inner layer comprising only component (a) and an outer layer comprising components (a) and (b).

7. The process as claimed in claim 1, wherein the coated catalyst comprises a plurality of layers with an inner layer and an outer layer each comprising the components (a) and (b); and the component (a) in the inner layer has a higher specific surface area than the component (a) in the outer layer.

* * * * *